US008084648B2

(12) United States Patent
Buchanan et al.

(10) Patent No.: US 8,084,648 B2
(45) Date of Patent: Dec. 27, 2011

(54) PROCESS FOR PRODUCING CYCLOHEXYLBENZENE

(75) Inventors: John S. Buchanan, Lambertville, NJ (US); Jane C. Cheng, Bridgewater, NJ (US); Tan-Jen Chen, Kingwood, TX (US); James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 8 days.

(21) Appl. No.: 12/747,295

(22) PCT Filed: Jan. 13, 2009

(86) PCT No.: PCT/US2009/030787
§ 371 (c)(1),
(2), (4) Date: Aug. 10, 2010

(87) PCT Pub. No.: WO2009/102517
PCT Pub. Date: Aug. 20, 2009

(65) Prior Publication Data
US 2010/0317895 A1    Dec. 16, 2010

Related U.S. Application Data

(60) Provisional application No. 61/027,971, filed on Feb. 12, 2008.

(51) Int. Cl.
C07C 45/53 (2006.01)
C07C 37/08 (2006.01)
C07C 2/68 (2006.01)

(52) U.S. Cl. ......... 568/346; 568/631; 568/798; 585/467

(58) Field of Classification Search .................. 568/346, 568/361, 798; 585/467
See application file for complete search history.

(56) References Cited

U.S. PATENT DOCUMENTS

| | | | |
|---|---|---|---|
| 3,412,165 A | 11/1968 | Slaugh et al. | |
| 3,536,771 A | 10/1970 | Graff | |
| 3,760,018 A | 9/1973 | Suggitt et al. | |
| 3,760,019 A | 9/1973 | Crone, Jr. et al. | |
| 3,784,618 A | 1/1974 | Suggitt et al. | |
| 3,839,477 A | 10/1974 | Suggitt et al. | |
| 3,957,687 A | 5/1976 | Arkell et al. | |
| 3,962,362 A | 6/1976 | Suggitt | |
| 4,021,490 A | 5/1977 | Hudson | |
| 4,094,918 A | 6/1978 | Murtha et al. | |
| 4,122,125 A | 10/1978 | Murtha et al. | |
| 4,152,362 A | 5/1979 | Murtha | |
| 4,177,165 A | 12/1979 | Murtha et al. | |
| 4,206,082 A | 6/1980 | Murtha et al. | |
| 4,219,689 A | 8/1980 | Murtha | |
| 4,268,699 A | 5/1981 | Murtha et al. | |
| 4,329,531 A | 5/1982 | Murtha et al. | |
| 4,439,409 A | 3/1984 | Puppe et al. | |
| 4,447,554 A | 5/1984 | Murtha et al. | |
| 4,826,667 A | 5/1989 | Zones et al. | |
| 4,954,325 A | 9/1990 | Rubin et al. | |
| 5,236,575 A | 8/1993 | Bennett et al. | |
| 5,250,277 A | 10/1993 | Kresge et al. | |
| 5,334,795 A | 8/1994 | Chu et al. | |
| 5,362,697 A | 11/1994 | Fung et al. | |
| 5,557,024 A | 9/1996 | Cheng et al. | |
| 6,077,498 A | 6/2000 | Diaz Cabanas et al. | |
| 6,489,529 B1 | 12/2002 | Cheng et al. | |
| 6,506,953 B1 | 1/2003 | Cheng et al. | |
| 6,730,625 B1 | 5/2004 | Chang et al. | |
| 6,936,744 B1 | 8/2005 | Cheng et al. | |
| 2004/0092757 A1 | 5/2004 | Oguchi et al. | |
| 2005/0158238 A1 | 7/2005 | Tatsumi et al. | |
| 2008/0027256 A1 | 1/2008 | Roth et al. | |
| 2008/0027259 A1 | 1/2008 | Roth et al. | |
| 2008/0045768 A1 | 2/2008 | Roth et al. | |
| 2011/0037022 A1 | 2/2011 | Dakka et al. | |

FOREIGN PATENT DOCUMENTS

| | | |
|---|---|---|
| EP | 0 293 032 | 11/1988 |
| EP | 0 338 734 | 10/1989 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | 2009/038900 | 3/2009 |

OTHER PUBLICATIONS

I. Borodina et al., "Hydroalkylation of Benzene and Ethylbenzene over Metal Containing Zeolite Catalysts", Microporous and Mesoporous Materials, 2007, vol. 105, pp. 181-188.
W. Fan et al., "Synthesis and Catalytic Properties of a New Titanosilicate Molecular Sieve with the Structure Analogous to MWW-type Lamellar Precursor", Journal of Catalyst, 2006, vol. 243, pp. 183-191.
S. Kim et al., "Structural Evolution of B-MCM-36 and B-ITQ-2 from B-MCM-22", Bull. Korean Chem. Society, 2006, vol. 27, No. 10, pp. 1693-1696.
S. Lawton et al., "Zeolite MCM-49: A Three-Dimensional MCM-22 Analogue Synthesized by in Situ Crystallization", Journal of Physical Chemistry, 1996, vol. 100, pp. 3788-3798.
S. Maheshwari et al., "Layer Structure Preservation During Swelling, Pillaring, and Exfoliation of a Zeolite Precursor", Journal of American Chemical Soc., 2008, vol. 130, pp. 1507-1516.

(Continued)

Primary Examiner — Sikarl Witherspoon
(74) Attorney, Agent, or Firm — Jamie L. Sullivan

(57) ABSTRACT

In a process for producing cyclohexylbenzene, hydrogen and a liquid feed comprising benzene are introduced into a reaction zone and are contacted in the reaction zone under hydroalkylation conditions to produce cyclohexylbenzene. An effluent stream comprising cyclohexylbenzene and unreacted benzene is removed from the reaction zone and is divided into at least first and second portions, wherein the mass ratio of the effluent stream first portion to the effluent stream second portion is at least 2:1. The effluent stream first portion is then cooled and the cooled effluent stream first portion is recycled to the reaction zone.

22 Claims, 2 Drawing Sheets

OTHER PUBLICATIONS

J. Ruan et al., "*Structure Elucidation of the Highly Active Titanosilicate Catalyst Ti-YNU-1*", Angew. Chem. Int. Ed., 2005, vol. 44, pp. 6719-6723.

L. Slaugh et al., "*Hydrodimerization of Benzene to Phenylcyclohexane over Supported Transition Metal Catalysts*", Journal of Catalysis, 1969, vol. 13, pp. 385-396.

P. Wu et al., "*Methodology for Synthesizing Crystalline Metallosilicates with Expanded Pore Windows Through Molecular Alkoxysilylation of Zeolitic Lamellar Precursors*", Journal of American Chemical Soc., 2008, vol. 130, pp. 8178-8187.

L. Zhicheng et al., "*Static Synthesis of High-Quality MCM-22 Zeolite with High $SiO_2/Al_2O_3$ Ratio*", Chinese Science Bull, 2004, vol. 49, No. 6, pp. 556-561.

PROCESS FOR PRODUCING CYCLOHEXYLBENZENE

CROSS-REFERENCE TO RELATED APPLICATIONS

This application claims the benefit of prior U.S. provisional Application Ser. No. 61/027,971 filed Feb. 12, 2008, and is a National Stage Application of International Application No. PCT/US2009/030787 filed Jan. 13, 2009, which is hereby incorporated by reference in its entirety.

FIELD OF THE INVENTION

The present invention relates to a process for producing cyclohexylbenzene and optionally converting the resultant cyclohexylbenzene into phenol and cyclohexanone.

BACKGROUND OF THE INVENTION

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam and nylon 6.

It is known from U.S. Pat. No. 5,053,571 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. The hydroalkylation reaction is carried out at a liquid hourly space velocity (LHSV) ranging from 1 to 100, a reaction pressure ranging from 100 to 1000 kPa, a hydrogen feed rate ranging from 0.2 to 6 mole per mole of feedstock per hour, and a reaction temperature ranging from 100 to 300° C.

In addition, U.S. Pat. No. 5,146,024 discloses that benzene can be reacted with hydrogen in the presence of carbon monoxide and a palladium-containing zeolite X or Y to produce cyclohexylbenzene, which can then be converted in high yield to phenol and cyclohexanone by autooxidation with subsequent acid treatment. The hydroalkylation reaction is carried out at a liquid hourly space velocity (LHSV) of the benzene feed of about 1 to about 100 hr$^{-1}$, a total reaction pressure of about 345 to about 10,350 kPa, a molar ratio of $H_2$ to benzene of about 0.1:1 to about 10:1, a molar ratio of carbon monoxide to $H_2$ of about 0.01:1 to about 0.3:1, and a temperature of about 100 to about 250° C. Preferred operating conditions are said to include a LHSV of the benzene feed of about 5 to about 30 hr$^{-1}$, a total reaction pressure of about 1,380 to about 4,830 kPa, a molar ratio of $H_2$ to benzene of about 0.2:1 to about 1:1, a molar ratio of CO to $H_2$ of about 0.02:1 to about 0.1:1, and a reaction temperature of about 140 to about 200° C.

U.S. Pat. No. 6,037,513 discloses that cyclohexylbenzene can be produced by contacting benzene with hydrogen in the presence of a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the peroxide decomposed to the desired phenol and cyclohexanone.

However, although benzene hydroalkylation is an attractive route for the production of cyclohexylbenzene, with current processes the selectivity to the desired cyclohexylbenzene product at conversions above 30% is generally less than 70%. The major impurities in the product are cyclohexane and dicyclohexylbenzene. Cyclohexane builds up in the $C_6$ recycle stream and must be removed by treatment or purging, whereas the dicyclohexylbenzene by-product requires transalkylation. Although transalkylation of dicyclohexylbenzene with benzene produces additional cyclohexylbenzene product, the cost of transalkylation is not insignificant. There is therefore a need to provide a benzene hydroalkylation process with improved selectivity to monocyclohexylbenzene.

U.S. Pat. No. 3,784,617 discloses a process for the hydroalkylation of mononuclear aromatic compounds, in which an aromatic charge and a first portion of hydrogen are reacted in a first stage to produce a partially hydroalkylated stream and, after cooling, the partially hydroalkylated stream and a second portion of hydrogen are reacted in a second stage to produce a hydroalkylate product. Introducing the hydrogen in multiple stages reduces the degree of benzene conversion, and hence the temperature rise, in each stage. By avoiding excessive temperature increases, more favorable product selectivities are said to be obtained.

According to the present invention, it has now been found that cooling and recycling of part of the effluent from the hydroalkylation reaction zone, with or without staged addition of hydrogen, allows improved temperature control such that the hydroalkylation process can be operated at or near isothermal conditions and the selectivity to the desired monocyclohexylbenzene can be maximized.

SUMMARY OF THE INVENTION

In one aspect, the invention resides in a process for producing cyclohexylbenzene, the process comprising:

(a) introducing hydrogen and a liquid feed comprising benzene into a reaction zone;

(b) contacting the benzene with the hydrogen in the reaction zone under hydroalkylation conditions to produce cyclohexylbenzene;

(c) removing an effluent stream comprising cyclohexylbenzene and unreacted benzene from said reaction zone;

(d) dividing the effluent stream into at least first and second portions;

(e) cooling the effluent stream first portion; and (f) recycling the cooled effluent stream first portion to the reaction zone;

wherein the ratio of the mass of the effluent stream first portion to the mass of the effluent stream second portion is at least 2:1.

Conveniently, the ratio of the mass of the effluent stream first portion to the mass of the effluent stream second portion is at least 3:1, preferably at least 4:1.

Conveniently, the cooling (e) reduces the temperature of the effluent stream first portion by at least 10 degrees C., such as at least 20 degrees C., for example at least 30 degrees C.

Conveniently, any difference in temperature between the liquid feed introduced into the reaction zone and the effluent stream removed from the reaction zone is less than 60 degrees C., preferably less than 40 degrees C.

Conveniently, the molar ratio of the hydrogen introduced into the reaction zone to the benzene in the liquid feed is between about 0.15:1 and about 15:1, for example from about 0.3:1 to about 1:1.

Conveniently, the reaction zone contains a catalyst comprising at least one molecular sieve and at least one hydrogenation metal. In one embodiment, said at least one molecular sieve is selected from zeolite beta, mordenite, zeolite X, zeolite Y and a molecular sieve of the MCM-22 family. In another embodiment, said at least one hydrogenation metal is selected from palladium, ruthenium, nickel, zinc, tin, and cobalt.

In one embodiment, the process further comprises recovering cyclohexylbenzene from the effluent stream second portion.

In another embodiment, the effluent stream second portion is fed to at least one further reaction zone where unreacted benzene in the effluent stream second portion is contacted with further hydrogen under hydroalkylation conditions to produce further cyclohexylbenzene. In some embodiments, the effluent stream second portion comprises unreacted hydrogen and the unreacted hydrogen is fed with the effluent stream second portion to said at least one further reaction zone, or the unreacted hydrogen is separated from the effluent stream second portion and then recycled to the first reaction zone or fed to said at least one further reaction zone.

DETAILED DESCRIPTION OF THE INVENTION

Figure 1:
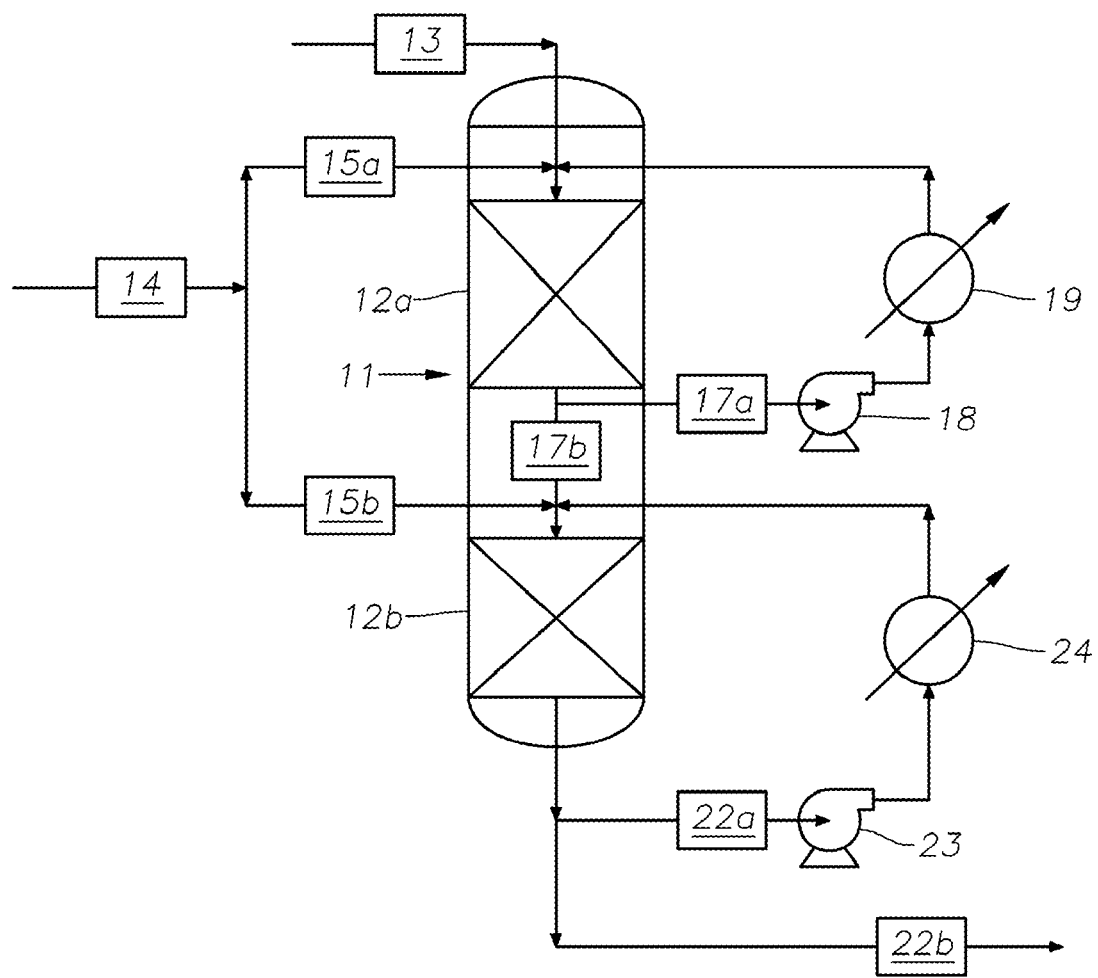
FIG. 1 is a diagram of a two-stage reactor for performing the benzene hydroalkylation process of Example 1.

Described herein is a process for the hydroalkylation of benzene to produce cyclohexylbenzene and then the conversion of the cyclohexylbenzene to cyclohexanone and phenol. Insofar as the hydroalkylation step produces dicyclohexylbenzene in addition to the desired monocyclohexylbenzene product, the process can include the further step of transalkylating the dicyclohexylbenzene with additional benzene to produce further monocyclohexylbenzene product.

Benzene Hydroalkylation

The first step in the present process comprises contacting hydrogen and a liquid feed comprising benzene with a hydroalkylation catalyst in at least one reaction zone under hydroalkylation conditions whereby the benzene undergoes the following reaction to produce cyclohexylbenzene (CHB):

Competing reactions include the complete saturation of the benzene to produce cyclohexane, dialkylation to produce dicyclohexylbenzene and reorganization/alkylation reactions to produce impurities, such as methylcyclopentylbenzene (MCPB). Although dicyclohexylbenzene can be transalkylated to produce additional CHB product, conversion to cyclohexane represents loss of valuable feed, whereas impurities such as methylcyclopentylbenzene (MCPB) are particularly undesirable since the boiling point of MCPB is very close to that of CHB so that it is very difficult to separate MCPB from CHB. It is therefore important to maximize the selectivity to cyclohexylbenzenes in the hydroalkylation reaction.

One of the factors that is important in maximizing the selectivity to cyclohexylbenzenes is reaction temperature, with lower temperatures generally favoring the production of the desired cyclohexylbenzenes. However, the hydroalkylation of benzene is exothermic and hence it is important to limit the temperature rise in the hydroalkylation step. In the present process this is achieved by dividing the liquid effluent stream from the hydroalkylation reaction zone into at least first and second portions and then cooling the effluent stream first portion, conveniently by at least 10 degrees C., preferably by at least 20 degrees C., for example at least 30 degrees C., and then recycling the cooled liquid effluent stream first portion, but not the effluent stream second portion, to the reaction zone. By ensuring that the ratio of the mass of the cooled effluent stream first portion recycled to hydroalkylation reaction zone to the mass of the effluent stream second portion is at least 2:1, such as at least 3:1, for example at least 4:1, the increase in temperature in the reaction zone during the hydroalkylation reaction can preferably be maintained at less than 60 degrees C., such as less than 40 degrees C. In this respect, the increase in temperature in the reaction zone during the hydroalkylation reaction is defined as the difference between the temperature of the benzene-containing liquid feed entering the reaction zone and the temperature of the liquid effluent stream removed from the reaction zone.

Typically, the effluent stream comprises unreacted benzene in addition to the desired cyclohexylbenzene and the effluent stream second portion is fed to at least one further reaction zone where the unreacted benzene is contacted with further hydrogen under hydroalkylation conditions to produce further cyclohexylbenzene. As in the case of the first-mentioned reaction zone, the temperature rise in the further reaction zone is conveniently controlled by cooling part of the liquid effluent from the further reaction zone by at least 10 degrees C., conveniently by at least 20 degrees C., for example at least 30 degrees C., and then recycling the cooled liquid effluent to the further reaction zone.

In some embodiments, the effluent stream second portion comprises unreacted hydrogen and the unreacted hydrogen is fed with the effluent stream second portion to said at least one further reaction zone, or the unreacted hydrogen is separated from the effluent stream second portion and then recycled to said first-mentioned reaction zone or fed to said at least one further reaction zone.

Any commercially available benzene feed can be used in the present hydroalkylation process, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 weight ppm, such as less than 500 ppm, for example less than 100 ppm, water. The total feed typically contains less than 100 weight ppm, such as less than 30 ppm, for example less than 3 ppm sulfur. The total feed generally contains less than 10 weight ppm, such as less than 1 ppm, for example less than 0.1 ppm, nitrogen. In preferred embodiments, the content of all three impurities (water, sulfur, nitrogen) is restricted to within any combination of the ranges specified above, The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Generally, the molar ratio of the hydrogen introduced into the or each reaction zone to the benzene in the liquid feed to the or each reaction zone is between about 0.15:1 to about 15:1, for example from about 0.3:1 to about 1:1, such as between about 0.4:1 to about 0.9:1. Suitable temperatures for the hydroalkylation reaction are between about 100° C. and about 250° C., such as between about 120° C. and about 200° C. Suitable reaction pressures are between about 100 and about 7,000 kPaa, such as between about 500 and about 5,000 kPaa.

The hydroalkylation reaction may employ for example a bifunctional catalyst comprising a molecular sieve and a hydrogenation metal. Preferably the molecular sieve is selected from zeolite beta, mordenite, zeolite X, zeolite Y and a molecular sieve of the MCM-22 family. Zeolite beta and its synthesis are disclosed in, for example, U.S. Pat. No. 3,308,069. Zeolite Y is a naturally occurring material but is also available in synthetic forms, such as Ultrastable Y (USY) and Dealuminized Y (DealY). Low sodium Ultrastable Y molecular sieve (USY) is described in U.S. Pat. Nos. 3,293,192 and 3,449,070. Dealuminized Y zeolite (DealY) may be prepared by the method found in U.S. Pat. No. 3,442,795. Zeolite UHP-Y is described in U.S. Pat. No. 4,401,556. Mordenite is also a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the present hydroalkylation catalyst although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present in the catalyst is selected such that the molar ratio of the aluminum in the molecular sieve to the hydrogenation metal is from about 1.5 to about 1500, for example from about 75 to about 750, such as from about 100 to about 300.

The hydrogenation metal may be directly supported on the molecular sieve, eg the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The effluent portion that is not employed as the cooled recycle stream may be treated to obtain the desired products. Thus the unreacted aromatic feed may be recovered by distillation and recycled to the alkylation reactor. The bottoms from the benzene distillation may be further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. and/or a pressure of about 800 to about 3500 kPa and/or a weight hourly space velocity of about 1 to about 10 hr$^{-1}$ on total feed and/or a benzene/dicyclohexylbenzene weight ratio of about 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This may be accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is preferably conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount of from 0.0001 mol % to 15 wt %, such as from 0.001 to 5 wt %, of the cyclohexylbenzene.

Suitable conditions for the oxidation step include a temperature between about 70° C. and about 200° C., such as about 90° C. to about 130° C. and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase. The cleavage may be effected, for example, at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The invention will now be more particularly described with reference to following non-limiting Examples and the accompanying drawings.

EXAMPLE 1

Two-Stage Benzene Hydroalkylation

Referring to FIG. 1, a two-stage reactor system suitable for conducting the present hydroalkylation process includes a reaction vessel 11 comprising first and second fixed catalyst beds 12(a), 12(b) respectively connected in series. All the fresh benzene used in the process is supplied to the first catalyst bed 12(a) as a liquid through inlet 13, whereas the hydrogen feedstream 14 is divided into two parts and supplied equally to the first and second catalyst beds 12(a), 12(b) through lines 15(a), 15(b) respectively. Some or all of the hydrogen supplied through line 15(a) reacts with part of the benzene in the first catalyst bed 12(a) to form cyclohexene, which quickly alkylates either benzene or cyclohexylbenzene, forming either cyclohexylbenzene or dicyclohexylbenzene. The remainder of the hydrogen converts benzene all the way to cyclohexane. Trace byproducts are not considered in this model. Thus a first liquid effluent stream exits the first catalyst bed 12(a) composed mainly of unreacted benzene together with lesser amounts of cyclohexylbenzene, dicyclohexylbenzene and cyclohexane.

The first liquid effluent stream is split into two (first and second) portions 17(a), 17(b). The (first) effluent stream first portion 17(a) is recirculated by a pump 18 through a heat exchanger 19, which lowers the temperature of stream 17(a), to the inlet 13, where the first portion 17(a) is mixed with the fresh benzene and hydrogen entering the first catalyst bed 12(a). The (first) effluent stream second portion 17(b) is combined with the hydrogen in line 15(b) and fed to the second catalyst bed 12(b) where at least part of the unreacted benzene is converted into additional cyclohexylbenzene, dicyclohexylbenzene and cyclohexane, which exit the second catalyst bed 12(b) as a second liquid effluent stream. The second liquid effluent stream is split into two (first and second) portions 22(a), 22(b). The (second) effluent stream first portion 22(a) is recirculated by a pump 23 and cooled by a heat exchanger 24 before being combined with the (first) effluent stream second portion 17(b) and the hydrogen 15(b) entering the second catalyst bed 12(b). The (second) effluent stream second portion 22(b) is removed for recovery of the desired cyclohexylbenzene product.

In one simulated example of the production of cyclohexylbenzene using the apparatus of FIG. 1, 3.0 g-moles/hr of benzene and 1.11 moles/hr hydrogen are fed to the reaction vessel 11, with half of the hydrogen being supplied to the first catalyst bed 12(a) and half being supplied to the second catalyst bed 12(b). The benzene is supplied to the first catalyst bed 12(a) at 150° C. and by, arranging that the mass ratio of the recirculating (first) effluent stream first portion 17(a) to the (first) effluent stream second portion 17(b) is 3:1 and that the (first) effluent stream first portion 17(a) is cooled to 120° C. in the heat exchanger 19, the first catalyst bed 12(a) is maintained under adiabatic conditions, that is the temperature of the (first) effluent stream second portion 17(b) is 150° C. The conversion of hydrogen in the first catalyst bed 12(a) is about 92%, whereas the conversion of benzene is about 16%.

By controlling the mass ratio of the recirculating (second) effluent stream first portion 22(a) to the (second) effluent stream second portion 22(b) at 3:1 and by cooling the (second) effluent stream first portion 22(a) to 121.4° C. in the heat exchanger 24, the second catalyst bed 12(b) is also maintained under adiabatic conditions, that is the temperature of the (second) effluent stream second portion 22(b) is 150° C. The conversion of hydrogen in the second catalyst bed 12(b) is about 85% and the conversion of benzene is about 18%. With two reaction stages, the final product, the (second) effluent stream second portion 22(b), contains 25.2 wt % of cyclohexylbenzene, 5.0 wt % dicyclohexylbenzene and 1.0 wt % of cyclohexane. The overall conversion of hydrogen and benzene is 92 and 31%, respectively.

EXAMPLE 2

Three-Stage Benzene Hydroalkylation

Figure 2:
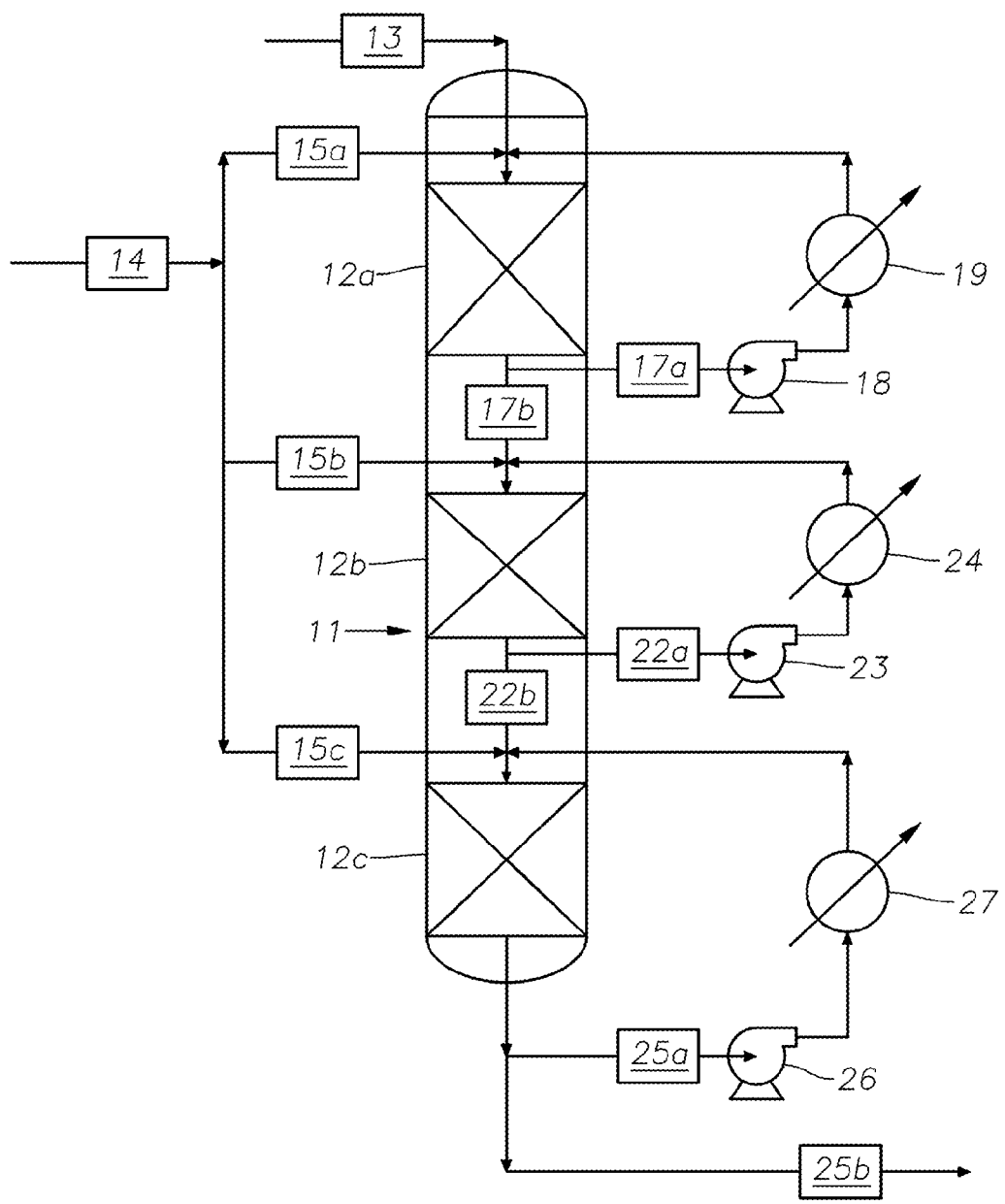
FIG. 2 is a diagram of a three-stage reactor for performing the benzene hydroalkylation process of Example 2.

FIG. 2 illustrates a three-stage reactor system suitable for conducting the present hydroalkylation process and employs like numerals to indicate like components to the system of FIG. 1. In particular, the system of FIG. 2 includes a reaction vessel 11 comprising first, second and third fixed catalyst beds 12(a), 12(b) 12(c) respectively connected in series. As in Example 1, all the fresh benzene used in the process is supplied to the first catalyst bed 12(a) as a liquid through inlet 13. However, the hydrogen feedstream 14 is now divided into three parts and supplied equally to the catalyst beds 12(a), 12(b), 12(c) through lines 15(a), 15(b), 15(c) respectively.

The first and second catalyst beds 12(a) and 12(b) of the system of FIG. 2 also include provision for recirculating and cooling portions 17(a) and 22(a) of their respective liquid effluents through respectively pumps 18 and 23, and heat exchangers 19 and 24. However, the (second) effluent stream second portion 22(b) is now is combined with the hydrogen in line 15(c) and fed to the third catalyst bed 12(c) where at least part of the unreacted benzene is converted into additional cyclohexylbenzene, dicyclohexylbenzene and cyclohexane, which exit the second catalyst bed 12(b) as a third liquid effluent stream. The third liquid effluent stream is split into two (first and second) portions 25(a), 25(b), with one portion 25(a) being recirculated and cooled by a pump 26 and heat exchanger 27 before being combined with the (second) effluent stream second portion 22(b) and the hydrogen 15(c) entering the third catalyst bed 12(c). The other portion 25(b) of the third effluent stream is removed for recovery of the desired cyclohexylbenzene product.

In one simulated example of the production of cyclohexylbenzene using the apparatus of FIG. 2, 3.0 g-moles/hr of benzene and 1.11 moles/hr hydrogen are fed to the reaction vessel 11. The benzene is supplied to the first catalyst bed 12(a) at 150° C. and by, arranging that the mass ratio of the recirculating (first) effluent stream first portion 17(a) to the (first) effluent stream second portion 17(b) is 3:1 and that the (first) effluent stream first portion 17(a) is cooled to 129° C. in the heat exchanger 19, the first catalyst bed 12(a) is maintained under adiabatic conditions, that is the temperature of the (first) effluent stream second portion 17(b) is 150° C. The conversion of hydrogen in the first catalyst bed 12(a) is about 94%, whereas the conversion of benzene is about 11%.

The second catalyst bed 12(b) is also maintained under adiabatic conditions by controlling the mass ratio of the recirculating (second) effluent stream first portion 22(a) to the (second) effluent stream second portion 22(b) at 3:1 and by cooling the (second) effluent stream first portion 22(a) to 129.7° C. in the heat exchanger 24. The conversion of hydrogen in the second catalyst bed 12(b) is about 89% and the conversion of benzene is about 12%.

The third catalyst bed 12(c) is also maintained under adiabatic conditions by controlling the mass ratio of the recirculating (third) effluent stream first portion 25(a) to the (third) effluent stream second portion 25(b) at 3:1 and by cooling the (third) effluent stream first portion 25(a) to 132.5° C. in the heat exchanger 27. The conversion of hydrogen in the second catalyst bed 12(b) is about 80% and the conversion of benzene is about 12%.

With three reaction stages, the final product, the (third) effluent stream second portion 25(b), contains 25.6 wt % of cyclohexylbenzene, 4.9 wt % dicyclohexylbenzene, and 0.9 wt % cyclohexane. The overall conversion of hydrogen and benzene is 92 and 31%, respectively. Comparing these results with those of Example 1, it will be seen that increasing the number of stages in the benzene hydroalkylation step can increase the selectivity to cyclohexylbenzene and reduce the selectivity to dicyclohexylbenzene and cyclohexane byproducts.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising:
   (a) introducing hydrogen and a liquid feed comprising benzene into a reaction zone;
   (b) contacting the benzene with the hydrogen in the reaction zone under hydroalkylation conditions to produce cyclohexylbenzene;
   (c) removing an effluent stream comprising cyclohexylbenzene and unreacted benzene from said reaction zone;
   (d) dividing the effluent stream into at least first and second portions;
   (e) cooling the effluent stream first portion; and
   (f) recycling the cooled effluent stream first portion to the reaction zone;
wherein the ratio of the mass of the effluent stream first portion to the mass of effluent stream second portion is at least 2:1.

2. The process of claim 1, wherein the ratio of the mass of the effluent stream first portion to the mass of the effluent stream second portion is at least 3:1.

3. The process of claim 2, wherein the ratio is at least 4:1.

4. The process of claim 1, wherein the cooling (e) reduces the temperature of the effluent stream first portion by at least 10 degrees C.

5. The process of claim 4 wherein the temperature is reduced by at least 20 degrees C.

6. The process of claim 1, wherein any difference in temperature between the liquid feed introduced into the reaction zone and the effluent stream removed from said reaction zone is less than 60 degrees C.

7. The process of claim 6 wherein the temperature difference is less than 40 degrees C.

8. The process of claim 1, wherein the molar ratio of the hydrogen to the benzene introduced into to the reaction zone is from 0.15:1 to 15:1.

9. The process of claim 8 wherein the ratio is from 0.3:1 to 1:1.

10. The process of claim 1, wherein the reaction zone contains a catalyst comprising at least one molecular sieve and at least one hydrogenation metal.

11. The process of claim 10, wherein said at least one molecular sieve is selected from zeolite beta, mordenite, zeolite X, zeolite Y and a molecular sieve of the MCM-22 family.

12. The process of claim 10, wherein said at least one molecular sieve has an X-ray diffraction pattern including d-spacing maxima at 12.4±0.25, 6.9±0.15, 3.57±0.07 and 3.42±0.07 Angstrom.

13. The process of claim 10, wherein said at least one molecular sieve is selected from MCM-22, PSH-3, SSZ-25, ERB-1, ITQ-1, ITQ-2, MCM-36, MCM-49, MCM-56, UZM-8, and mixtures of any two or more thereof.

14. The process of claim 10, wherein said at least one hydrogenation metal is selected from palladium, ruthenium, nickel, zinc, tin and cobalt.

15. The process of claim 1, wherein the hydroalkylation conditions include a temperature of 100 to 400° C. and/or a pressure of from 100 to 7000 kPaa.

16. The process of claim 1 and further comprising recovering cyclohexylbenzene from the effluent stream second portion.

17. The process of claim 1, wherein at least part of the effluent stream second portion is fed to at least one further reaction zone where the unreacted benzene in the effluent stream second portion is contacted with further hydrogen under hydroalkylation conditions to produce further cyclohexylbenzene.

18. The process of claim 17, wherein said at least part of the effluent stream second portion is cooled before being fed to said at least one further reaction zone.

19. The process of claim 13, wherein the effluent stream second portion comprises unreacted hydrogen and the unreacted hydrogen is fed to said at least one further reaction zone.

20. The process of claim 13, wherein the effluent stream second portion comprises unreacted hydrogen and the unreacted hydrogen is separated from the effluent stream second portion and then recycled to the first reaction zone or fed to said at least one further reaction zone.

21. A method for coproducing phenol and cyclohexanone, the method comprising producing cyclohexylbenzene by the process of claim 1, oxidizing the cyclohexylbenzene to produce cyclohexylbenzene hydroperoxide and cleaving the cyclohexylbenzene hydroperoxide to produce phenol and cyclohexanone.

22. A method for producing phenol, the method comprising producing cyclohexylbenzene by the process of claim 1, oxidizing the cyclohexylbenzene to produce cyclohexylbenzene hydroperoxide, cleaving the cyclohexylbenzene hydroperoxide to produce phenol and cyclohexanone, and dehydrogenating the cyclohexanone to produce further phenol.

* * * * *